Oct. 13, 1942. G. JANSSEN Plant Pat. 550
ROSE PLANT
Filed April 13, 1942
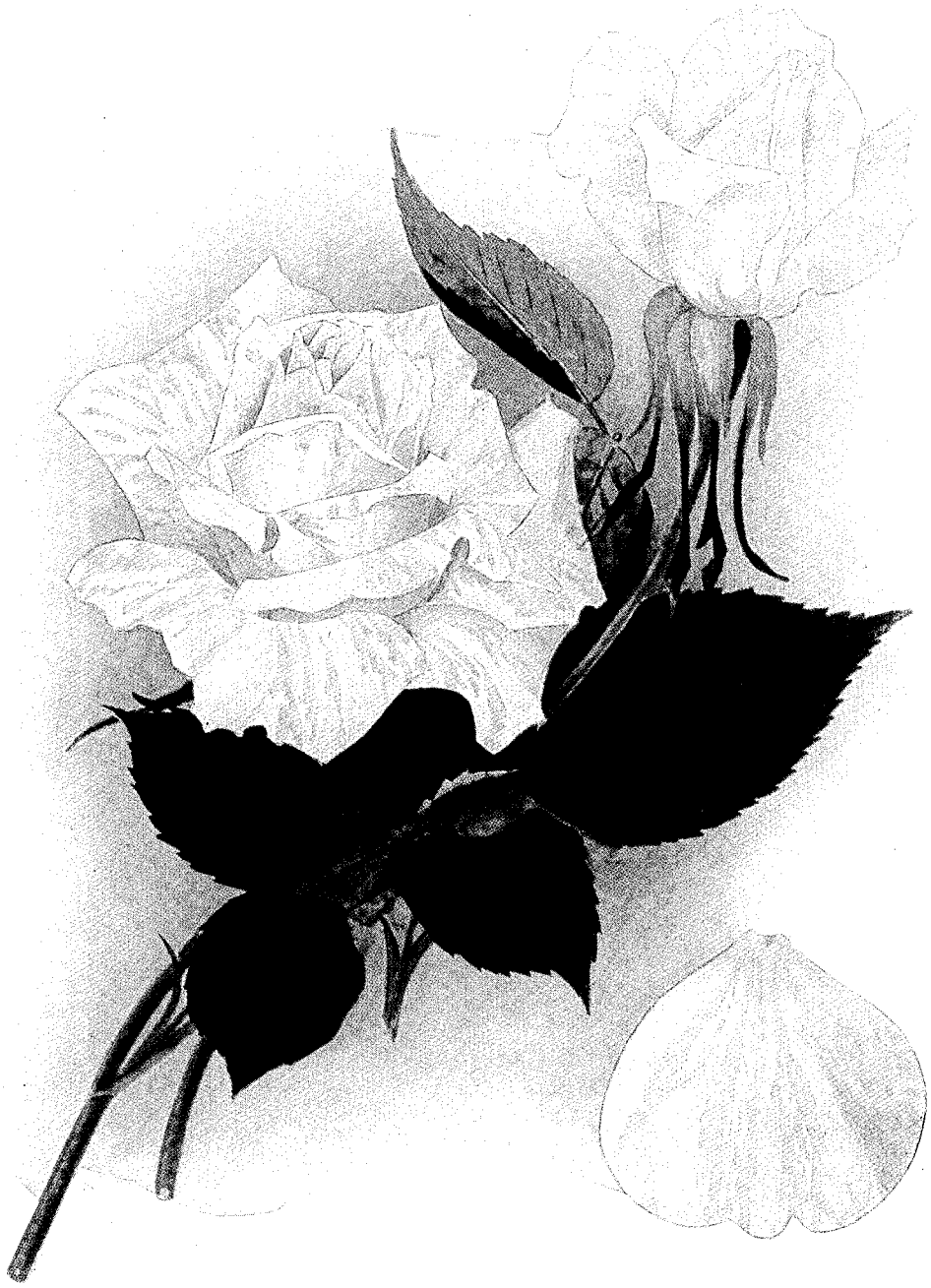
WITNESS
Addison E. Avery
George Janssen,
Inventor,
by Rummler Rummler & Davis,
Attorneys.

Patented Oct. 13, 1942

Plant Pat. 550

UNITED STATES PATENT OFFICE

550

ROSE PLANT

George Janssen, Chicago, Ill., assignor to The Premier Rose Gardens, Consolidated, Des Plaines, Ill., a corporation of Illinois Application April 13, 1942, Serial No. 438,803

1 Claim. (Cl. 47—61)

The new variety of rose plant herein described and illustrated is a sport of the well-known rose plant "Better Times." The buds of this sport bloom were asexually propagated by budding, have been rebudded numerous times and have come back true to the original sport bloom; thereby perpetuating the novel characteristics in the progeny.

The unusual characteristic of this new variety resides in its lavish display of variegated colors. The vivid, velvety cerise color of each petal, slashed in longitudinal stripes on a background that is a shade of pink tinted white, gives it a staunch, royal appearance. It has a most cheerful aspect.

The original painting shows the new rose in its natural colors and in the approximate size of the flower and bud. A single petal is also shown to illustrate the characteristic marking and color distribution.

This new variety in plant structure is similar to the parent plant "Better Times" except for its brilliant variegated coloring. It has all the good habits of "Better Times"; the long compact bud with long sepals hooding the petals until the bud begins to open; the breadth and depth of the full-blown flower with large petals and compact, high center; and its freedom from disease, fungus and insects. The petioles and peduncles are strong, sturdy, and practically thornless. The foliage is of attractive texture and color. The leaves are a dark green color, with inconspicuous ribs and veins.

One of the outstanding characteristics of the new rose is the persistence of its petals in hanging on until they dry. The compact central grouping of petals, which stand out so prominently, remains solid until the bloom begins to fade. At this stage the petals do not turn brown but the intense cerise color seems to decrease in brilliance to a lavender-pink shade (which is still pleasing to the eye). Blooms that have been kept in a refrigerated atmosphere have retained this dense mass of petals for about three weeks, only the outer whorl of petals falling off.

The following is a detailed description of the new variety:

Parentage: Sport of "Better Times."
Classification: Hybrid tea.

*Flower*

Blooming habit: Recurrent and continuous.
*Size of bloom.*—4 to 5 inches in diameter and 2 inches in depth.
*Form.*—Very compact high center area.
*Stem.*—Strong and sturdy.
*Petalage.*—40 to 43. *Persistence.*—(hang on and dry) about 2 weeks on cut flower.
*Color.*—Variegated cerise and light tinted pink.
*Texture.*—Velvety and thick.
*Fragrance.*—Sweet and delicate.
*Very resistant* to rose diseases, fungus, and insects.
*Lasting quality.*—Good both on plant and as a cut flower.

Bud:
*Size.*—2 to 2¼ inches from base to tip.
*Form.*—Long, pointed.
*Sepals.*—Long, spatulate at ends.
*Calyx.*—Hoods the bud.

*Genital organs*

Stamens-anthers: In great mass of about ¾ inch in diameter.
*Color.*—Lemon-yellow.
*Arrangement.*—Massed around the pistils, standing well above the numerous red-tipped stigmas.
*Styles.*—Great mass.
*Stigma.*—Has cerise-colored tip.

Thorns: Seldom occurring on new plant (on main stem very few and weak).

*Plant*

Form: Bush.

The color designations according to "A Dictionary of Color by Maerz and Paul" are as follows:

| Part | Color | Plate | Letter | Number |
|---|---|---|---|---|
| Large outer petals: region at base of petals. | Pale green | 17 | K | 5 |
| Light colored body of petals | | 41 | E | 1 |
| Color at lower part of variegation | | 41 | I | 1 |
| Shading into | | 41 | L | 1 |
| Shading at upper part into. | | 1 | J | 6 |
| Center petals: deep tones in very center. | Cerise+ | 41 | L | 1 |
| | | 4 | J | 6 |
| Upper side of leaf | | 24 | J | 4 |
| Under side of leaf | Grey drab | 21 | B | 1 |
| Stem | Peridot | 22 | L | 6 |

The brilliant variegated colors of this rose, together with its size, superior keeping qualities, and resistance to disease, combine to make a spectacular commercial product.

Having thus disclosed the invention, I claim:

A new and useful variety of rose plant as herein shown and described, characterized particularly by its peculiar variegation of colors, and shape of bloom, the depth of the compact centrol area of the flower, the long bud, lack of thorns, and sturdy stems.

GEORGE JANSSEN.